Figure 5:
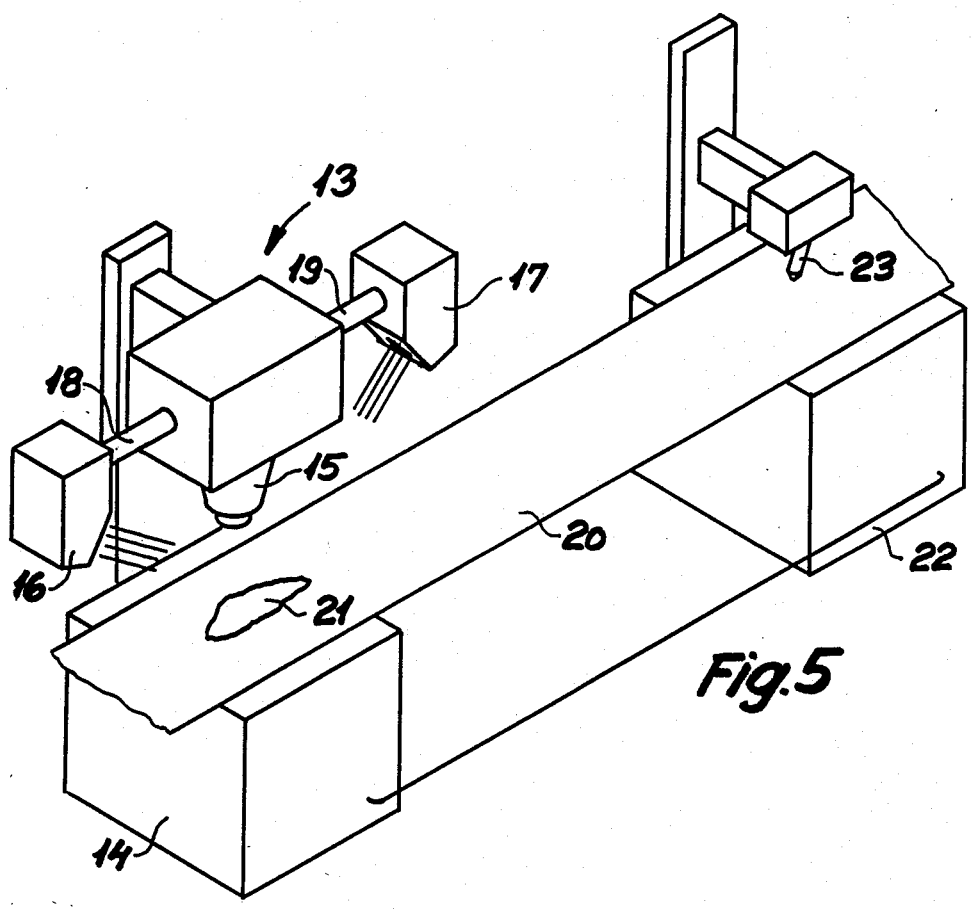

United States Patent [19]

Jensen et al.

[11] Patent Number: 4,908,703
[45] Date of Patent: Mar. 13, 1990

[54] METHOD OF MEASURING MEAT TEXTURE

[75] Inventors: Svend A. Jensen, Soborg; Peter Haagensen, Valby, both of Denmark

[73] Assignee: Lumetech A/S, Hellerup, Denmark

[21] Appl. No.: 216,620
[22] PCT Filed: Nov. 6, 1987
[86] PCT No.: PCT/DK87/00139
  § 371 Date: Jul. 6, 1988
  § 102(e) Date: Jul. 6, 1988
[87] PCT Pub. No.: WO88/03645
  PCT Pub. Date: May 19, 1988

[30] Foreign Application Priority Data

Nov. 6, 1986 [DK] Denmark ............... 5305/86

[51] Int. Cl.⁴ .................. G01N 21/88; G01N 33/12
[52] U.S. Cl. ..................... 358/106; 73/105; 356/237; 356/445; 426/231
[58] Field of Search .......... 358/101, 93, 106, 107; 73/104, 105; 356/237, 445; 426/231; 382/6, 8

[56] References Cited

U.S. PATENT DOCUMENTS

| | | | |
|---|---|---|---|
| 3,851,074 | 11/1974 | Gillespi | 426/231 |
| 3,877,818 | 4/1975 | Button | 356/416 |
| 4,226,540 | 10/1980 | Barten | 356/445 |
| 4,326,808 | 4/1982 | Pryor | 356/445 |
| 4,413,279 | 11/1983 | Görl | 358/107 |
| 4,439,037 | 3/1984 | Northeved | 356/445 |

FOREIGN PATENT DOCUMENTS

| | | |
|---|---|---|
| 0126492 | 11/1984 | European Pat. Off. . |
| 2843257 | 4/1979 | Fed. Rep. of Germany . |
| 3047490 | 10/1982 | Fed. Rep. of Germany . |
| 3413027 | 10/1985 | Fed. Rep. of Germany . |
| 341919 | 1/1972 | Sweden ............... 358/106 |

OTHER PUBLICATIONS

Search Report PCT/DK87/00139.

Primary Examiner—Howard W. Britton
Attorney, Agent, or Firm—Ladas & Parry

[57] ABSTRACT

In a method of detecting meat texture the surface of the meat is illuminated in at least two directions which are substantially perpendicular to a base for the meat in a common illumination plane. A loose texture manifests itself in deep cracks (8, 9, 10) in e.g. the fillet of fish. When the surface of the fillet is illuminated in the directions (11 and 12), the depressions (8, 9, 10) bring about such a great contrast in the recording of an image of the surface that the image information can be processed electronically and be utilized for control of equipment, either for rejection of the fillet or for cutting away the damaged areas.

4 Claims, 2 Drawing Sheets

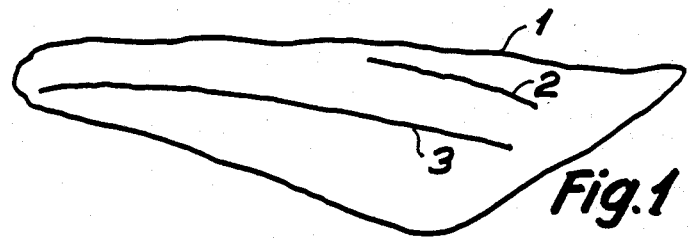
Fig. 1
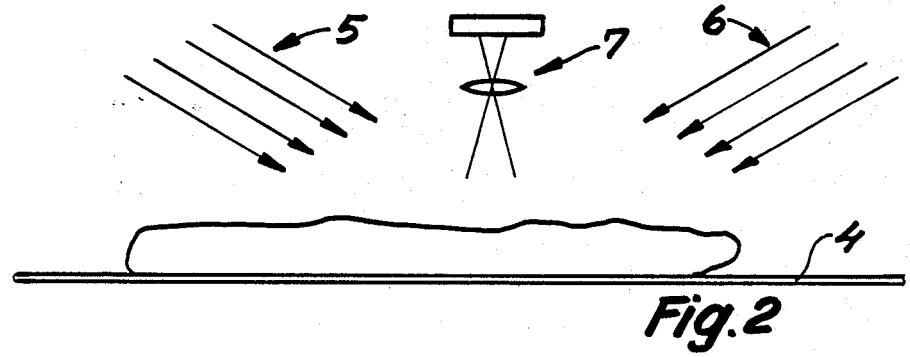
Fig. 2
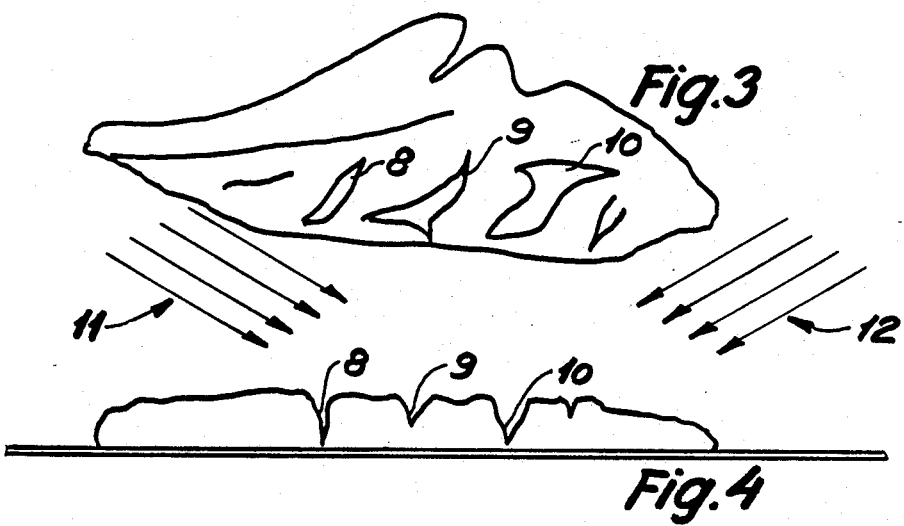
Fig. 3
Fig. 4

METHOD OF MEASURING MEAT TEXTURE

The invention concerns a method of detecting meat texture, i.e. the firmness and coherence of the meat. Today, cooking of food products takes place automatically to a great extent, so that meat with a loose texture can be torn to pieces and thus cannot any more be accepted as a first-class product.

The object of the invention is to provide a method by means of which the texture may be detected automatically and without contact while the meat, e.g. a fillet of fish, is advanced on a conveyor.

This is obtained by performing the method as stated in the characterizing portion of claim 1, it having been found that with correct setting of the said acute angles with respect to the size and the type of the cracks in the meat which must be expected in the measurement, a surprisingly reliable measure of the extent of such cracks transversely to said illumination plane may be achieved.

In connection with detection of quite different phenomena, such as microscopic cracks or measuring of outer contours, it is known to illuminate the object and to record the image information, see e.g. DE OS Nos. 2 843 257 and 3 413 027. This prior art is relatively sophisticated, using i.a. special wavelengths for the light, and in relation to this the invention consists in realizing that the opposite, viz. simplification of the art, lends itself particularly well precisely for detection of meat texture.

More particular, the relatively deep cracks in meat having a poor texture involves good contrast formation, in particular when the cracks extend predominantly transversely to a plane thorugh the sources of light.

When measuring the texture of fish meat, which is a primary object of the invention, it should be noted that cracks in the longitudinal direction of a fillet of fish, i.e. substantially in parallel with the longitudinal fibres, are not indicative of a loose texture, whereas cracks transversely to the longitudinal fibres directly indicate a loose texture and a poor meat quality. Accordingly, for measuring the texture of fish meat, the method is advantageously performed as stated in claim 2.

Thus, the invention is based on the finding that the above-mentioned illumination and image recording may be utilized as an expression of the texture of the meat, but the surprisingly good results are also due to a special utilization of the video information processing, known per se, for precisely this object. When the method is performed as stated in claim 3, the method may thus be improved additionally by using electronic contrast intensification, e.g. of the type disclosed in the book "From image to surfaces" by William Erik Leifur Grimson, M.I.T. 1981, p. 16-100.

The utilization of the digetal technique in connection with the invention also entails that the invention is preferably performed as stated in claim 4. The positional information thus provided is then transferred to e.g. a robot controlled water jet cutting apparatus which automatically cuts away the parts of the fillet where the meat is loose and incoherent.

The invention will be explained more fully by the following description of an embodiment with reference to the drawing, in which FIG. 1 schematically shows a fillet of fish having a satisfactory texture, FIG. 2 shows a section through the fillet from FIG. 1 and schematically shows an embodiment of illumination directions and recording direction for image information, FIG. 3 schematically shows a fillet of fish having a dissatisfactory texture, FIG. 4 is a section through FIG. 3 corresponding to FIG. 2, and FIG. 5 in principle shows an apparatus for performing the method of the invention.

In FIG. 1, the numeral 1 represents the contour of a fillet of fish having in the longitudinal direction some grooves 2, 3 in the meat substantially in parallel with the longitudinal direction of the fillet.

In FIG. 2, the fillet is shown resting on a base 4, and arrows 5, 6 indicate illumination directions for recording of image information by means of a video camera shown schematically at 7. Seen in the longitudinal direction of the fillet, the surface of the fish is relatively even and has only small elevations and depressions which will not result in a noticeable contrast to the shown illumination directions, which form predetermined acute angles with the base 4. In the embodiment shown, these illumination directions form substantially uniform acute angles with the base 4, which may vary, however, depending upon the type of meat which is to be examined. The optical axis of the image apparatus 7 will be essentially parallel with the illumination plane defined by the illumination directions 5 and 6 and be essentially parallel with the angle bisector for these illumination directions.

FIG. 3 shows a fillet of fish having a loose texture, which involves deep grooves or cracks 8-10 extending predominantly transversely to the longitudinal direction of the fillet. FIG. 4 shows the same as FIG. 3, but it is noted now that the illumination directions 11, 12 entail that dark regions occur in the bottom of the cracks 8-10, because the light falls as indicated by the broken lines in the figure. When an image is taken of the fillet from FIG. 4, information will thus be obtained on the extent of such transverse cracks.

It will be appreciated that the depth and the width and optionally a preferred inclination of the cracks to be detected are important for the selection of the optimum illumination directions 11 and 12. Thus, it is within the scope of the invention to change the illumination directions in accordance with the product to be examined. It will likewise be appreciated that several recordings may be taken on the same object with mutually differently positioned illumination planes and associated recording directions.

FIG. 5 schematically shows an apparatus for performing the method, comprising a recording station 13 mounted on a table 14 which preferably contains data processing equipment for processing the video information which is obtained by means of a camera. The recording equipment 13 may be adjustable in various ways, and the lamps 16, 17 shown are movably secured on a pair of arms 18, 19.

The numeral 20 represents a conveyor for fillets of fish, such as the fillet 21. As soon as an image of the surface of the fillet has been recorded, the video information is processed in the data processing equipment for producing texture information. The information may be displayed on a video display and may form the basis for automatic removal of the fillet from the conveyor if the quality is below a certain level. Alternatively, the image information may comprise positional information which is transferred to a cutting apparatus 22 with a cutting robot 23, which, e.g. by means of a water jet, cuts away precisely those portions of the fillet which have a too loose texture.

Thus, the method described permits fully automatic sorting or subsequent processing of fillets of fish so that a higher production rate and improved product quality are obtained.

We claim:

1. A method of detecting meat texture, characterized by illuminating the surface of the meat by means of angularly adjustable uniform sources of light in at least two directions which, in a common illumination plane substantially perpendicular to a base for the meat, form acute angles with the base, and producing image information of the illuminated surface by means of a single camera seen from an area in the vicinity of the illumination plane and the angle bisector plane for said illumination directions.

2. A method according to claim 1 and for detection of fish meat texture, characterized by placing the fish meat on the base so that the longitudinal fibres of the meat are parallel with the illumination plane.

3. A method according to claim 1, wherein the image information is produced by means of a video camera, characterized by intensifying contrasts in the image information by means of electronic signal processing, known per se, of the video information.

4. A method according to claim 3, characterized by producing from the image information positional information on image contrasts which are greater than a predetermined value.

* * * * *